US006387378B1

(12) United States Patent
Shibley et al.

(10) Patent No.: US 6,387,378 B1
(45) Date of Patent: *May 14, 2002

(54) DEVICE FOR STORAGE AND MUCOSAL DELIVERY OF BIOLOGICAL OR PHARMACEUTICAL MATERIALS TO ANIMALS

(76) Inventors: George P. Shibley; Karen K. Brown; Leszek J. Choromanski; Sharon A. Bryant, all of Miles Inc., Mobay Rd., Pittsburgh, PA (US) 15205-9741

( * ) Notice: Subject to any disclaimer, the term of this patent is extended or adjusted under 35 U.S.C. 154(b) by 0 days.

This patent is subject to a terminal disclaimer.

(21) Appl. No.: 08/118,905

(22) Filed: Sep. 9, 1993

(51) Int. Cl.[7] ...................... A61K 39/012; A61K 13/00; A61M 31/00; A61M 5/00

(52) U.S. Cl. .................... 424/273.1; 424/434; 424/435; 424/438; 424/422; 424/430; 424/184.1; 604/48; 604/77; 604/200; 604/187; 604/244; 514/2

(58) Field of Search ............................ 424/88–92, 422, 424/430, 434, 435, 273.1, 184.1; 604/48, 54, 77, 93, 131, 187, 200, 244; 514/2

(56) References Cited

U.S. PATENT DOCUMENTS

| | | | | | |
|---|---|---|---|---|---|
| 2,059,966 | A | * | 11/1936 | Kaufman et al. | 604/200 |
| 2,066,868 | A | * | 1/1937 | Whittaker | 604/200 |
| 2,453,525 | A | * | 11/1948 | McNeill | 604/48 |
| 3,572,337 | A | * | 3/1971 | Schunk | 604/77 |
| 3,610,483 | A | * | 10/1971 | Visconti et al. | 604/48 |
| 3,716,133 | A | | 2/1973 | Koebler et al. | 206/534 |
| 3,743,104 | A | | 7/1973 | Peterson | 211/70.1 |
| 3,942,668 | A | | 3/1976 | Eberle et al. | 220/8 |
| 4,007,367 | A | * | 2/1977 | Rusteberg et al. | 435/2 |
| 4,014,991 | A | | 3/1977 | Baer et al. | 424/89 |
| 4,300,545 | A | * | 11/1981 | Goodnow et al. | 604/54 |
| 4,473,548 | A | * | 9/1984 | Frenkel et al. | 424/88 |
| 4,792,333 | A | | 12/1988 | Kidder | 604/83 |
| 5,026,342 | A | * | 6/1991 | Hammerstedt et al. | 435/2 |
| 5,045,313 | A | * | 9/1991 | Frenkel et al. | 424/88 |
| 5,102,783 | A | * | 4/1992 | Alkemade et al. | 435/2 |
| 5,190,880 | A | * | 3/1993 | Cassou et al. | 435/1 |
| 5,222,940 | A | * | 6/1993 | Wilk | 604/77 |

FOREIGN PATENT DOCUMENTS

| | | |
|---|---|---|
| EP | 458337 | 11/1991 |

* cited by examiner

*Primary Examiner*—Nita Minnifield
(74) *Attorney, Agent, or Firm*—William M. Blackstone

(57) ABSTRACT

Disclosed herein is a device for storing and/or delivering an effective amount of biological or pharmaceutical material to an animal comprising a tube disposed to contain said biological or pharmaceutical material and sealed at its ends and adapted to provide an opening through which the biological or pharmaceutical material exits and is administered to an intended site of the animal.

1 Claim, No Drawings

DEVICE FOR STORAGE AND MUCOSAL DELIVERY OF BIOLOGICAL OR PHARMACEUTICAL MATERIALS TO ANIMALS

BACKGROUND OF THE INVENTION

1. Field of the Invention

The present invention relates to a storage and mucosal delivery device for biological or pharmaceutical materials. More specifically, the present invention relates to a storage and mucosal delivery tube for administering biological or pharmaceutical materials to animals.

2. Brief Description of the Prior Art

Generally, it has been know to orally administer biological or pharmaceutical materials such as vaccines. The celebrated polio vaccine was orally administered by embedding it in sugar cube. Vaccines have been orally administered by metal gavage tubes connected to syringes or simply using a syringe without a needle attached thereto. U.S. Pat. No. 4,041,991 discloses a passive oral delivery system for a rabies vaccine to foxes by imbedding a bite-permeable hydrophobic plastic container into a bait and leaving the bait for the animals to eat and thus become immunized.

By the present invention, there is disclosed a device for storing and/or delivering a biologically or pharmaceutically effective amount of material to an animal.

SUMMARY OF THE INVENTION

In accordance with the foregoing, the present invention encompasses a device for storing and/or delivering an effective amount of biological or pharmaceutical material to an animal comprising a tube disposed to contain said biological or pharmaceutical material and sealed at its ends, and adapted to provide an opening through which the biological or pharmaceutical material exits and is administered to an intended site of the animal.

Also encompassed by the invention is a method of administering to an animal an effective amount of biological or pharmaceutical material by providing a tube disposed to contain said biological or pharmaceutical material, sealed at its ends, adapted to provide an opening through which the biological or pharmaceutical material exists and is administered to an intended site of the animal.

It has been found that by using the device of the invention, one is able to store effective amounts of biological or pharmaceutical materials such as vaccines, immunostimulants or drugs at ambient temperature or in a frozen condition and/or in liquid nitrogen. It has also been found that by the use of the device of the invention, one can actively administer the biological or pharmaceutical materials to animals. By the term "actively" herein is meant that the animals can be caused to take in a measured amount of the biological or pharmaceutical material. The device is further advantaged in that it is durable and takes little storage space in, say, a liquid nitrogen tank. This and other aspects of the invention are described more fully below.

DETAILED DESCRIPTION OF THE INVENTION

The device of the invention is a tube preferably a capillary tube which is of a material and construction that is safe to animals and is at the same time sufficiently durable to maintain its integrity under the service and environmental conditions of administration. Illustratively, the tube is made of a substrate which is flexible, preferably a flexible polymeric substrate which would not injure the animals tissue, but is sufficiently durable to withstand pressure from say biting, and as such prevents the biological or pharmaceutical material from spilling onto humans who would handle the device. An illustration but non-limiting example of the polymeric substrate can be polypropylene. The tube is of dimensions sufficient to contain the effective amount of the biological or pharmaceutical material and reach an intended site of administration. Illustratively, the tube can be of a volume from 0.1 to 5 mL and preferably 1.0 to 2 mL. Typically, the tube is impermeable. Preferably, it is sufficiently durable to withstand penetration from animal bits, breakage by dropping or the like.

In preparing the device, the tube containing a biological or pharmaceutical material is sealed at its ends ("end-seals") by heating or ultrasound techniques which are known in the art. In one embodiment of the invention, the tube is provided at the one end with a plug or the like means before the end-seal. As described more fully hereafter, the plug or the like provides a convenient means for using a plunger to expel the biological or pharmaceutical materials from the tube. It is, however, envisioned that the biological or pharmaceutical material can be expelled from the tube by other means. In a preferred embodiments of the invention, the plug is a material comprising cotton embedded in a chemical which can react with aqueous solutions to seal the tube in a section below the end-seal.

To exit the pharmaceutical or biological material, the tube is adapted to open by penetrating it effectively to release or expel the material. The tube can be penetrated by means such as cutting. Typically, the tube is first penetrated at a lower section and then at an upper section in order to effect a release of the biological or pharmaceutical material. As would be realized, upon cutting the tube, particularly a capillary tube, at the lower section, the biological or pharmaceutical material does not exit the tube. Consequently, spillage of the material and the associate negatives such as infection of humans can be avoided. Upon cutting the tube at the upper section, (below the plug the biological or pharmaceutical material is released. Alternately, upon cutting the tube above or through the plug, a plunger can be used to expel the biological or pharmaceutical material from the tube by pushing the plunger down the tube.

In the practice of the invention, the device can be used to deliver an effective amount of biological or pharmaceutical material to the animals. Illustratively, vaccines in liquid or frozen forms can be contained, stored and delivered in accordance with this invention. The device of the invention is more suitable than art-related devices, such as vials, in instances when vaccines must stay frozen during storage. For example, in using vials, a modified live *Toxoplasma gondii* (*T. gondii*) vaccine containing bradyzoites to prevent oocyst shedding in cats could not be stabilized in a liquid, frozen or lyophilized form. In using the device of the invention, said vaccine is effectively stored in a frozen form. In a specific embodiment of the invention, the stabilized vaccine preparation can be filled into tubes (straws) by a special closed-system filling machine manufactured by IMV-BICEF (France). The straws with a capacity of 0.5 mL were filled with at least 0.45 mL. This capacity allows the straw to deliver at least 0.4 mL of vaccine orally to the cat. Filled straws are frozen at a controlled rate of between 0.5° C. per minute to as much as 30° C. per minute until they reach a temperature of −40° C. At this point, the straws are loaded into containers which hold multiple straws and are plunged into liquid nitrogen. Such treatment allows storage of the vaccine for extensive periods of time. Table 1 shows a comparison of the results of freezing a *T. gondii* bradyzoite vaccine in straws with freezing the same vaccine preparation in conventional liquid nitrogen vials. It has been found that storage of *T. gondii* in straws is significantly better than storage of this organism in vials. The straws containing the above-mentioned Toxoplasmosis vaccine are stored in liquid nitrogen. Prior to vaccination of a cat, a straw is removed and thawed (at a temperature between 4° C. and 37° C.).

A convenient method of preparing the *T. gondii* vaccine can be as follows. The vaccine can be prepared by injecting mice with tachyzoites, allowing the tachyzoites to produce a chronic infection localized in the brains as tissue cysts containing bradyzoites and harvesting the tissue cysts with bradyzoites. The harvested tissue cysts are treated with pepsin to release the bradyzoites and then a stabilizer such as dimethyl sulfoxide (DMSO) is added to the resulting vaccine In delivering the vaccine to cats, the straw is provided with a means for exiting the vaccine. Typically, the exiting means is provided by cutting the straw at its bottom, followed by cutting it at the top (below the plug, if any) to release the vaccine, while the straw is positioned at or over the site of administration. Thus, a facile delivery of a vaccine is accomplished in a few seconds by simply inserting the bottom end of the straw into the cat's mouth and cutting off the top end of the straw just under the cotton plug.

In the embodiment of the invention wherein the device contains a plug, a plunger can be used to expel the vaccine from the straw. In this embodiment, after cutting off the bottom of the straw, one must cut the top of the straw typically at a point approximately at the mid-section of the plug. The plunger pushes against the plug forcing it down the straw. As the plug is pushed down the straw, it expels the vaccine into the animals mouth. A sleeve or the like means can be used to hold the straw. The sleeve would fit around the straw and preferably hold the straw onto a plunger mechanism.

It has been found that the use of the straw to vaccinate cats with the *T. gondii* vaccine works quite well whether one uses the special sleeve/plunger to expel the vaccine or just allows the vaccine to be released. Illustratively, straws from the preparations listed in Table 2 were thawed at room temperature and used to vaccinate cats by: 1) cutting off the bottom of the straw; 2) placing the straw into the cat's mouth; and 3) cutting the straw under the cotton plug to deliver the vaccine. All cats were seronegative for antibodies to *T. gondii* prior to the vaccination. Half of the cats were vaccinated and half the cats were left as non- vaccinated controls. At 28 days post one vaccination, all of the cats were bled and their sera were checked for antibodies via a direct agglutination test kit sold by Bio-Merieux, France. This test is specific for *T. gondii*. The results of vaccination are listed in Table 3 as a direct agglutination titer (reciprocal of the dilution of serum which was positive). All of the vaccinated cats responded to the vaccination. Since the control cats did not develop antibody titer, this indicates that there was no external exposure to *T. gondii*. Hence, the response of the vaccinated cats is confirmed to be a result of vaccination. The advantage of the device and the method of using the same is that more vaccine doses can be packaged in a smaller container, the straw is not breakable as is a vial, the contents of the straw can be the thawed quickly and there is no needle involved, thus making this a safe delivery system.

The invention is further illustrated but is not intended to be limited by the following examples in which all parts and percentages are by weight unless otherwise specified.

Comparison of Viability of Toxoplasma *Gondii* Stored Frozen in Cryovials of Straws Held in Liquid Nitrogen

TABLE 1

| SAMPLE | VIABLE TITER |
|---|---|
| *T.GONDII* BRADYZOITES + 15% DMSO (CRYOVIALS) | <3.2 |
| *T.GONDII* BRADYZOITES + 15% DMSO (STRAWS) | 200 |

Table 2 hereunder demonstrates a further evaluation of straws for storage of *T. gondii*. In this case bradyzoite preparations of *T. gondii* were evaluated for viability prior to addition of DMSO (Homogenate 1 hr at room temperature) and after addition of DMSO (vaccine preparation). These preparations were held at either room temperature (RT) or at 40° C. for various time periods. Holding the preparation at 40° C. for longer periods of time so that the DMSO can penetrate the organism seemingly helped to preserve viability during freezing of the vaccine preparation in the straws. This experiment demonstrates that the loss of viability of *T. gondii* after freezing is less than the loss of viability during incubation with the stabilizer (DMSO). It is also of interest that thawing the straws at 4° C. is preferable. It should be noted that if DMSO is not included in the vaccine preparation there is no viability remaining after freezing even when straws are used for storage.

TABLE 2

EVALUATION OF THE STRAW FREEZING PROCESS FOR *TOXOPLASMA GONDII*

| SAMPLE | TREATMENT | VIABILITY TITER |
|---|---|---|
| HOMOGENATE | 1 HOUR, RT | 42658 |
| HOMOGENATE + 12.5% DMSO | 1 HOUR, RT | 316 |
| HOMOGENATE + 12.5% DMSO | 2 HOUR, RT | 316 |
| HOMOGENATE + 12.5% DMSO | 4 HOUR, RT | 478 |
| HOMOGENATE + 12.5% DMSO | 6 HOUR, RT | 316 |
| HOMOGENATE + 12.5% DMSO | 4 HOUR, 4° C. | 1479 |
| HOMOGENATE + 12.5% DMSO | 24 HOUR, 4° C. | 6760 |
| HOMOGENATE + 12.5% DMSO IN STRAWS | FROZEN IN LIQUID N2 THAWED AT 4° C. | 10 |
| HOMOGENATE + 12.5% DMSO IN STRAWS | FROZEN IN LIQUID N2 THAWED AT 4° C. | 48 |
| HOMOGENATE + 12.5% DMSO IN STRAWS | FROZEN IN LIQUID N2 THAWED AT 4° C. | 68 |

TABLE 2-continued

EVALUATION OF THE STRAW FREEZING PROCESS FOR *TOXOPLASMA GONDII*

| SAMPLE | TREATMENT | VIABILITY TITER |
|---|---|---|
| HOMOGENATE + 12.5% DMSO IN STRAWS | FROZEN IN LIQUID N2 THAWED AT 4° C. | 100 |
| HOMOGENATE + 12.5% DMSO IN STRAWS | FROZEN IN LIQUID N2 THAWED AT 4° C. | 43 |
| HOMOGENATE + 12.5% DMSO IN STRAWS | FROZEN IN LIQUID N2 THAWED AT RT | 32 |
| HOMOGENATE + 12.5% DMSO IN STRAWS | FROZEN IN LIQUID N2 THAWED AT RT | 29 |
| HOMOGENATE + 12.5% DMSO IN STRAWS | FROZEN IN LIQUID N2 THAWED AT RT | 48 |
| HOMOGENATE + 12.5% DMSO IN STRAWS | FROZEN IN LIQUID N2 THAWED AT RT | 21 |
| HOMOGENATE + 12.5% DMSO IN STRAWS | FROZEN IN LIQUID N2 THAWED AT RT | 15 |

TABLE 3

| | | DIRECT AGGLUTINATION TITER | |
|---|---|---|---|
| CAT NO. | TREATMENT | PREVACCINATION | POST VACCINATION |
| 1299 | VACCINATION | <40 | >40 <4000 |
| 1301 | VACCINATION | <40 | >4000 |
| 1316 | VACCINATION | <40 | >4000 |
| 1322 | VACCINATION | <40 | >4000 |
| 1324 | VACCINATION | <40 | >4000 |
| 1297 | NONE (CONTROL) | <40 | <40 |
| 1298 | NONE (CONTROL) | <40 | <40 |
| 1300 | NONE (CONTROL) | <40 | <40 |
| 1303 | NONE (CONTROL) | <40 | <40 |
| 1307 | NONE (CONTROL) | <40 | <40 |

<40 indicates that the cat is seronegative.
>40 indicates that the cat has responded to the vaccination.

The foregoing demonstrate the use of the device of the invention to store a vaccine in liquid nitrogen.

While the invention has been described with specificity as to oral delivery of biological or pharmaceutical materials such as *T gondii* vaccine, it is also envisioned that the device can be used for any vaccination of mucosal membranes. For instance, the device can be used for vaginal vaccination, intraocular vaccination and intranasal vaccination in addition to oral vaccination. The device can be used to deliver any other modified live, attenuated or inactivated vaccine which can stimulate an immune response via the mucosal vaccination route. Additionally, the device can be used to deliver other liquid preparations such as immunostimulants or drugs which must be delivered to mucosal surfaces.

From the foregoing, it will be apparent that additional changes and modifications of the invention may be made within the spirit and scope of the claimed invention and are intended to be included in the scope of the claims as recited below.

What is claimed is:

1. A method of delivering an effective amount of a liquid *T. gondii* vaccine to an animal by providing a tube containing said *T. gondii* vaccine, which tube is sealed at its ends, and administering the vaccine to an intended location on the animal by first piercing the sealed tube at its lower section to create an opening, placing the opening at the location where the vaccine is to be administered, and thereafter piercing the tube at its upper section to release the vaccine from the lower section opening.

* * * * *